United States Patent
Guthrie et al.

(10) Patent No.: US 6,409,686 B1
(45) Date of Patent: *Jun. 25, 2002

(54) VIRTUAL PROBE FOR A STEREOTACTIC DIGITIZER FOR USE IN SURGERY

(75) Inventors: Barton L. Guthrie, Birmingham, AL (US); Robert A. Daniels, Haverhill, MA (US)

(73) Assignee: Sherwood Services AG, Shaffhausen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/549,752

(22) Filed: Apr. 14, 2000

Related U.S. Application Data

(63) Continuation of application No. 08/847,308, filed on Apr. 24, 1997, now Pat. No. 6,120,465, which is a continuation of application No. 08/521,908, filed on Aug. 31, 1995, now abandoned, which is a continuation of application No. 08/185,716, filed on Jan. 24, 1994, now abandoned.

(51) Int. Cl.$^7$ ................................................ A61B 5/00
(52) U.S. Cl. ...................................................... 600/587
(58) Field of Search ........................ 128/922; 600/459, 600/461, 587, 595; 604/117; 606/130

(56) References Cited

U.S. PATENT DOCUMENTS

| | | | |
|---|---|---|---|
| 3,933,148 A | * | 1/1976 | Wyler et al. |
| 4,058,114 A | * | 11/1977 | Soldner |
| 4,722,336 A | | 2/1988 | Kim et al. |
| 4,791,934 A | | 12/1988 | Brunnett |
| 5,056,523 A | | 10/1991 | Hotchkiss, Jr. et al. |
| 5,186,174 A | | 2/1993 | Schlondorff et al. |
| 5,230,623 A | | 7/1993 | Guthrie et al. |
| 5,257,998 A | * | 11/1993 | Ota et al. ............... 606/130 |
| 5,305,203 A | | 4/1994 | Raab |
| 5,309,913 A | | 5/1994 | Kormos et al. |
| 5,792,146 A | | 8/1998 | Cosman |
| 5,848,967 A | | 12/1998 | Cosman |
| 6,006,126 A | | 12/1999 | Cosman |
| 6,120,465 A | | 9/2000 | Guthrie et al. |
| 6,122,341 A | | 9/2000 | Butler et al. |
| 6,122,541 A | | 9/2000 | Cosman et al. |

\* cited by examiner

*Primary Examiner*—Max Hindenburg

(57) ABSTRACT

This invention relates to a three-dimensional digitizer and a probe means associated with said digitizer that enables a virtual target point to be visualized and depth and range measurements to that target to be determined. In one embodiment, a mechanical articulated arm or other type of 3-D digitizer is used in conjunction with a graphics workstation which displays images from CT, MR, or other scanning means of the anatomy. By registration of the digitizer to the patient's physical anatomy, a representation of the digitizer on the display means of the graphics workstation is possible. The position of the digitizer will be displayed in its quantitative relationship to the patient's anatomy, including internal pathologies such as tumors. The end means of the 3-D digitizer could be a holder or fixation device which can accept a sliding probe. The probe, for example, could be a shaft which slides in a spring-loaded or non-spring-loaded fashion within the fixation means of the digitizer. The degree of extension of the probe from the fixation means can be read out by a scale, which might be engraved on the shaft of the sliding probe. The digitizer, when calibrated to the anatomy, would register a target point and also a direction of the probe as it would approach that point, as seen on the graphics workstation. There may be a pre-determined relationship of the virtual tip of a probe relative to the fixation means as it scans the anatomy with the probe moving in space. The physical probe might be the sliding rod, which will be retractile within the fixation means. Thus, by knowing the degree of retraction, one can gauge the distance from the tip of the sliding probe to the virtual target, as calculated in the 3-D graphic workstation.

12 Claims, 1 Drawing Sheet

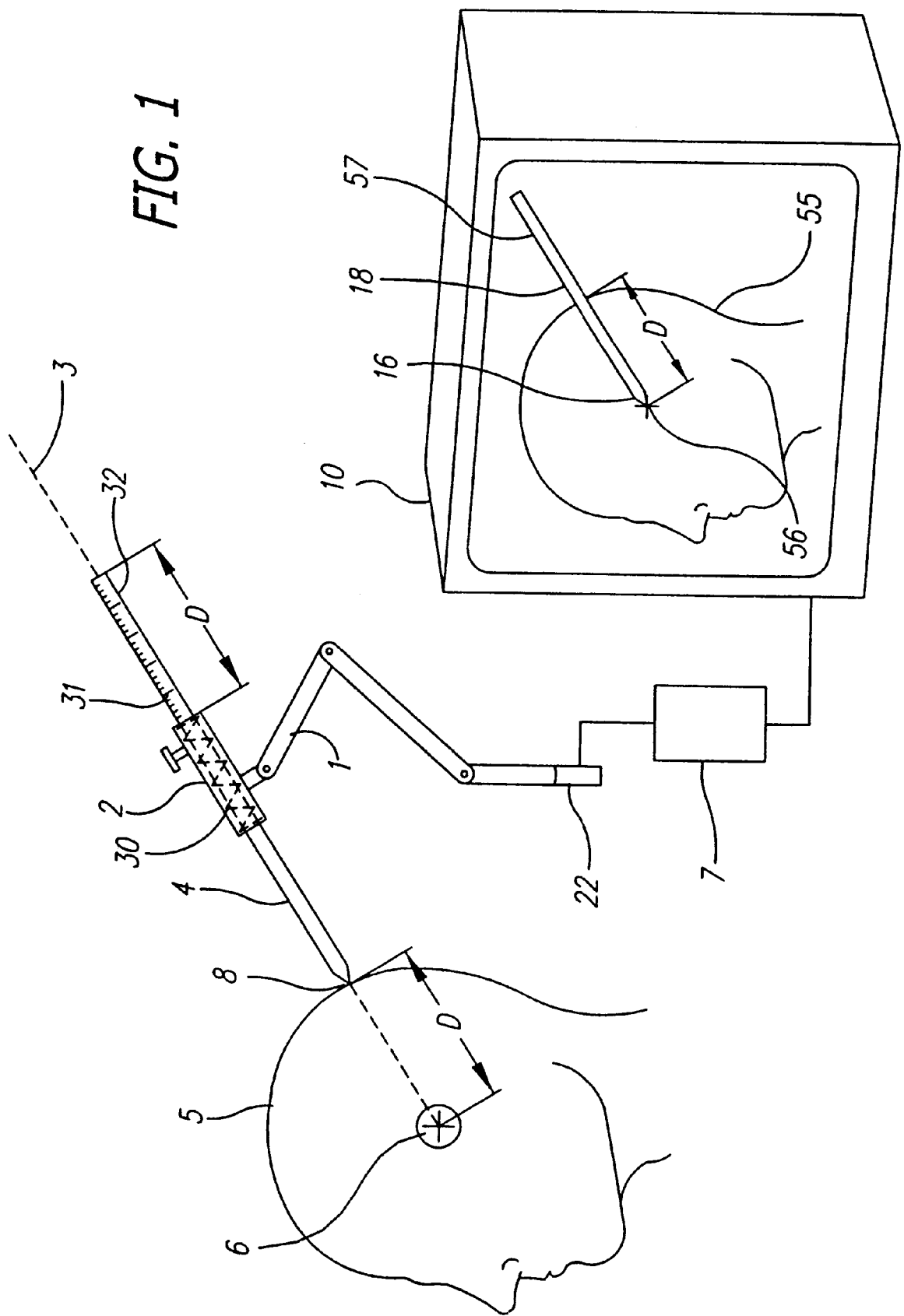

VIRTUAL PROBE FOR A STEREOTACTIC DIGITIZER FOR USE IN SURGERY

This application is a Continuation in Part of prior application Ser. No. 08/847,308 filed on Apr. 24, 1997 now U.S. Pat. No. 6,120,465, which is a Continuation of prior application Ser. No. 08/521,908, filed on Aug. 31, 1995 abandoned, which is a Continuation of prior application Ser. No. 08/185,716 filed on Jan. 24, 1994 abandoned.

DESCRIPTION OF THE PRIOR ART

The use of stereotactic frames and three-dimensional digitizers in so-called "frameless" stereotaxy is now well known and described in the literature. In the case of frame-based stereotaxy, typically a head ring is placed on the patient, usually his head, and an arc system is further attached to the head ring so as to direct a probe into the body quantitatively to achieve an internal target, such as a tumor. In a case of frameless stereotaxy, several types of three-dimensional digitizers, including mechanically articulated arms, optically coupled probes, electromagnetic coupling devices, ultrasonic and acoustic devices have been devised which give the operator a frameless and freehand means of identifying a target within the physical anatomy by relating the position of a navigator to a graphic representation of that anatomy derived from scanner image data. For example, a CT X-ray scan of the patient's head may be done, and a set of two-dimensional scan slices may be collected and inputted into a computer graphic workstation. The workstation can then assemble these 2-D slices and render the anatomy in a three-dimensional representation, shown on the display means of the computer workstation, such as a cathode ray tube (CRT). By identifying at least three non-colinear points on the physical anatomy, as relates to the 3-D representation in the computer graphic workstation, one can register the entire data set in the computer workstation relative to the actual anatomy. By using a digitizer or navigator which has an encoding means to give position data of a navigator in real space back to the computer graphic workstation, and by touching a known point on a navigator to the three non-colinear points on the physical anatomy in a calibration maneuver, the digitizer may be calibrated relative to the anatomy and its position can be displayed on the computer graphic workstation display means as a virtual indication of the position and orientation of the digitizer. This is a standard technique in the field of so-called frameless stereotaxy.

There are several types of digitizers which can be used for this purpose, and they range from mechanically encoded arms, optically coupled devices, electromagnetically coupled devices, ultrasonically coupled devices, and other technologies. To this date, theses digitizers involved a probe or instrument means which is attached to the digitizer, so that when the probe tip is pointed to physical anatomy, the position of the tip on the three-dimensional graphics of the anatomy in the computer workstation can be represented. Various instrument holders can be applied to the digitizer to hold probes, suction tubes, forceps, and other instruments, and they may have a known calibrated length so as so make the mapping between physical and graphic space.

One of the objects of this invention is to enable the operator to use the digitizer to point at an internal target in the physical anatomy without having to attach a rigid or fixed probe means to the digitizer, so as to give a virtual presentation of where the digitizer would be pointing in the physical anatomy along a given probe line, without actually physically reaching that internal target point. It is notable that if one has a fixed probe of predetermined or calibrated length in the digitizer, and that probe is pointing along a line projected through a target, it is not immediately obvious by mechanical means what the distance between the probe tip and the desired anatomical target is. The probe tip may be placed, for example, on the external anatomy such as the scalp, pointing in the direction towards an internal target such as a tumor, and it would be desirable to know by an immediate physical observation what the distance from the scalp to the tumor is along the projected line of the probe. This could be calculated or visualized on the computer graphic workstation, but a physical visualization on the digitizer or probe means would be desirable. It is an object of the present invention to provide such mechanical means on the digitizer probe means.

DESCRIPTION OF THE FIGURES

FIG. 1 shows an embodiment of the present invention which includes a virtual sliding probe means on a digitizer with 3-D graphic workstation cooperatively coupled to the digitizer.

DESCRIPTION OF THE INVENTION

FIG. 1 shows one embodiment of the present invention. A digitizer, represented by a mechanically encoded arm 1 is connected by electronic means 7 to a computer graphic workstation 10. The digitizing arm has lengths of known values and encoded joints, so that the position of probe adaptor 2 can be tracked relative to a base or holding structure 22 and the movement of probe holder 2 relative to 22 can therefore be tracked in three-dimensional space. The interface electronic 7 is designed to assimilate the electronic encoder data from the digitizer 1 and enable it to be represented in the computer graphic workstation 10. In the probe holder 2 is a probe means 4, such as a solid rod or pointer. Its tip 8 may be touching the external anatomy of a patient 5, and the projection of the axis of the probe 3 may pass through an internal anatomical point 6, which is at a distance (D) away from tip 8. The representation of the patient's anatomy may be displayed by Figure 55 by assimilating image scan data and representing it as described above in a two-dimensional or three-dimensional display. The target point may be determined in this three-dimensional display and represented as points 56 on the display. If the digitizer 1 has built into its predetermined calculation a standardized length of probe means to be inserted into the end adaptor 2, then the tip of the predetermined-length probe may be represented by point 16 on a graphic rendering of the probe means 57 on the display means. In many cases of application of this type of digitizer, however, it is desirable to plan the position and orientation of the digitizer applicator 2 relative to the patient's anatomy 5 and an internal target 6 prior to actually making an incision in the patient's scalp at point 8. In this situation, the standard probe length would be unacceptable in some situations to orient the adaptor 2, since, if it were in place in the adaptor 2, it would achieve the anatomical target 6. It would have to actually penetrate through the external anatomy and into the interior of the body. Of course, the adaptor means 2, with no probe inserted, could be moved around freehand and in space, and thus the position tracked on a computer graphic workstation, so as to give an appreciation of a direction towards the target and, as displayed on the computer graphic workstation, a sense of the physical distance between point 16 and 18 on the computer rendering, which would be, for example, the depth from the external anatomy to the target point 56 along the projected line 3.

As described in FIG. 1, it is possible to insert a probe means into adaptor 2, so as to indicate mechanically the direction of the digitizer axis 3 and to indicate the point of contact of direction 3 to the external anatomy at point 8, and yet not require that the probe have a fixed calibrated length which would correspond to achieving the internal target 6. Instead, as shown in FIG. 1, the probe 4 can be a movable, sliding means, such as a rod which slides within a channel or opening in adaptor 2. The rod may either be a free-sliding rod or it can be biased by an internal spring 30, which is inside of adaptor 2 and enables a restoring force or spring-loaded bias on probe 4. In this way, as adaptor 2 is advanced or withdrawn in distance from point 8 at the external anatomy, the sliding probe 4 would extend or withdraw inside of guide adaptor 2. The probe 4 might be of a predetermined length, such that when it is at an initial position within adaptor 2, its length corresponds to a pre-determined length associated with the digitizer calibration. As the sliding probe 4 withdraws further into adaptor 2, there may be a readout scale means 31 associated or cooperatively coupled to the rod that gives the rod's relative position or differential movement relative to adaptor 2. In this way, the distance (D) from the anatomical target (6), which corresponds to the virtual endpoint of the pre-calibrated probe length, to the external contact point 8 could be read out by the extension distance, or scale reading, of a portion 32 of the sliding means. Thereby, the operator can visually see, on a mechanical adaption to the digitizer, the scale reading 31 which is the distance (D) from the external anatomy to a target within a depth of the patient's body. This same distance (D) might also correspond to the associated visualized projection distance between the virtual probe tip graphic 16 and the graphic representation of the external anatomy point 18.

Thus, by freehand movement of the digitizer 1 with the sliding probe 4 as one moves the digitizer in space relative to the anatomy 5, having the sliding probe 4 contact the external anatomy, the operator, without having to visualize the computer graphic workstation, could simply read out scale 31 and have an immediate sense of the depth of the virtual probe tip (for the standardized probe length) relative to the external contact point 8.

The scale or readout means 31 could be at various locations or in various forms, as associated with the adaptor 2. FIG. 1 shows a simple scale 31 on the tail end of a probe. The scale would be at the patient proximal end 4 of the probe. The scale might read the degree of extension (D) directly or it could indicate the length of extension of the probe proximally or directly the distance from a reference point on adaptor 2 to the physical probe tip at surface contact 8. The distance or scale measurements could be represented electronically by a digital translation readout or it could be a side carrier with millimeter scale and not directly engraved onto the probe shaft itself. The invention is intended to include all such variations of a mechanically or electromechanically derived scale reading on a sliding probe relative to the adaptor means 2 on a digitizer.

The sliding probe means could have a variety of forms, shapes, or adaptations. It might be spring-loaded, as indicated in FIG. 2 or it could be simply a friction or sliding fit through a guide channel or groove in adaptor 2. It may be an instrument such as a suction tube, coagulating tube, or merely a rod means as a measuring device. The scale means could be adapted to any of these applications.

One of the utilities of this type of device is that by freehand or frameless movement of the digitizer wand and its adaptor 2 in space, one gets an immediate appreciation as the probe direction 3 changes of the relative distance of the tip of proximal element 4 of the probe to a virtual target 6 within the anatomy. There might be other holder means in space which probe 4 slides into that could freeze the orientation of probe line 3 as a point to the anatomy 6. Once the appropriate orientation has been positioned as seen by the representation of the probe 57 on the graphics, the guide means (not shown in FIG. 1) can be locked in place, the distance (D) observed from the scale 31, and the digitizer with the probe removed from the holder means to a rest position. Thereby the holder means can be used pass other instruments into the body, and knowledge of the displacement from the external anatomy 8 to the target 6 will have been mechanically determined by said reading on the scale 31.

There are many variations of the embodiment shown in FIG. 1 which are intended to be included within this invention. The schematized three-dimensional digitizer 1 is shown as a mechanical arm, but it could involve position and orientation detection means which span a wide range of physical principles. Optical, ultrasonic, electromagnetic, and other coupling means are possible to be substituted for a mechanically coupled arm. The adaptor means 2 could take many shapes and forms, including holes within blocks, v-grooves, channels of various types, and the slider probe 4 could also take a variety of shapes, including simple cylindrical rods, bars, tools in elongated shapes, such as electrocautery or suction devices, endoscopes, etc. The computer graphic workstation represented by 10 is shown schematically as a cathode ray tube structure, but it could have liquid crystal display and be in other forms associated with modern computer technology. The method of use of this invention could also take various forms. The probe holder 2 with slider probe 4 could be, in a freehand and fluid way, moved around in the location of the patient's anatomy of interest while the operator reviews the relationship of the probe in graphic form 57 relative to the anatomy 55 on the computer graphic workstation 10. The virtual probe tip 16 can be moved in a real time and interactive fashion within the anatomy while the slider probe tip 8 is contacting continuously the external surface of the body. When an optimal orientation of the graphic rendering of the probe 57 is seen, the operator could observe the scale reading 31 and have an instantaneous perception of the depth and the orientation of the probe direction 3. This would provide a convenient way of marking the surface point or entry point for an optimal probe direction, represented by point 8. At that point, the entire three-dimensional digitizer could be removed from the field, and a surgical intervention could be conducted based on that entry point. The knowledge of the scale reading 31 could then provide knowledge of the depth (D) from the entry point 8 to the actual target location 6, which is represented by the virtual probe tip 16 corresponding to the target 56 on the graphic display means of the computer graphic graphic workstation 10. All this could be done in real time and interactively. Various display means on the computer graphic workstation could be provided, including orthogonal sectional views through the anatomy, probe's eye view and the plane-of-probe view, various other reconstructive planes, and the forms of the image data could be various. CT, MRI, ultrasound, PET, SPECT: all could be forms of scanning which could be rendered simultaneously or individually on the computer display.

Having described the invention above, what we claim by U.S. Letters Patent are the following:

1. Apparatus for determining probe depths within a human body by means of computer graphic assisted stereotaxy, comprising:

a probe adapter;

a slide probe adapted to be coupled to and slide with respect to said probe adapter along a line parallel to a probe direction defined by said probe adapter, said slide probe having a slide probe tip which is adapted to contact portions of said anatomy;

readout means cooperatively coupled to said slide probe to provide a distance readout corresponding to the distance of said slide probe tip with respect to said probe adapter;

a freehand three-dimensional digitizer coupled to said probe adapter, said digitizer adapted to provide position data corresponding to said probe direction and a predetermined probe tip position and corresponding to a position of said slide probe tip relative to said probe adapter, said position data further being defined with respect to the anatomy of a patient when said three-dimensional digitizer is calibrated in position relative to said anatomy;

computing means in communication with said three-dimensional digitizer, said computing means configured to
  (i) display on display means said position of said slide probe tip relative to said probe adapter and said probe direction in relation to said anatomy; and
  (ii) accept scanner image data of said anatomy;

whereby in use when said three-dimensional digitizer is near said anatomy, said probe direction and said probe tip can be moved to a desired position relative to said anatomy and a desired target in said anatomy as represented on said display means, and said distance readout of said readout means can be a gauge of the depth from said slide probe tip to said target when said slide probe tip contacts a part of said anatomy.

2. The apparatus of claim 1, wherein said three-dimensional digitizer is one of a mechanically encoded arm, an optically coupled device, an electromagnetically coupled device, and an ultrasonically coupled device.

3. The apparatus of claim 1, wherein said slide probe is a rod-like probe with a distance scale that is cooperatively connected to said slide probe such that when said slide probe moves with respect to said probe adapter, said distance scale provides a measure of the relative position of said slide probe relative to said probe adapter whereby said depth of said slide probe tip with respect to said target can be read off of said scale.

4. The apparatus of claim 3, wherein said distance scale provides a measure of the distance from the external anatomy to the target.

5. The apparatus of claim 3, wherein said distance scale is one of an electronic digital translation readout scale, and a slide carrier coupled to a millimeter scale.

6. An apparatus for facilitating performance of a surgical procedure, which comprises:
  a probe;
  a probe holder for holding the probe and defining a probe axis of direction, the probe holder adapted to permit movement of the probe relative to the probe holder along the probe axis of direction to thereby assume a predetermined relative position of the probe relative to the probe holder;
  a digitizer for providing position data with respect to an anatomical portion of a patient and relating to the probe axis of direction and to the predetermined relative position of the probe; and
  a computer for processing image scan data of an anatomical portion of a patient and for accepting the positional data, and having a display for displaying an image corresponding to the predetermined relative position of the probe and the probe axis of direction relative to the anatomical portion.

7. The apparatus according to claim 6 including readout indicia associated with the probe for determining the predetermined relative position of the probe to thereby provide an indicator relating to a distance between the probe and an internal target within the anatomical portion.

8. A distance determining apparatus for use with a three-dimensional digitizer having a probe adapter, the digitizer providing positional data corresponding to a direction of the probe adapter and a position of the probe adapter with respect to a patient's anatomy, and with the positional data being inputted to a computer graphic workstation having a display that displays the predetermined tip end position and the predetermined probe adapter direction, the distance determining apparatus comprising:
  (a) a depth probe mechanically coupled to the probe adapter and movable with respect to the probe adapter along a line parallel to the direction, the depth probe having a end adapted to contact portions of the patient's anatomy; and
  (b) a readout associated with the probe for indicating a relative position of the probe relative to the probe adapter whereby in use when the three-dimensional digitizer is near the anatomy, the direction and position of the probe adapter can be moved relative to the anatomy and a desired target in the anatomy as represented on the computer graphic workstation display, and the readout is a gauge of the depth from the probe end to the target when the probe contacts a part of the anatomy.

9. The apparatus of claim 8 wherein the probe is a rod-like probe with a distance scale that is cooperatively connected to the probe such that when the probe moves with respect to the probe adapter, the distance scale provides a measure of the relative position of the depth probe relative to the probe adapter whereby the depth of the probe end with respect to the target can be read off of the distance scale.

10. The apparatus of claim 8 wherein the probe is spring loaded with respect to the probe adapter so that when the probe contacts the anatomy, the probe can retract within the probe adapter freely and with a spring bias so that it will tend to continuously contact anatomy as the three-dimensional digitizer is passed over the anatomy, thereby providing a continuous indication of the distance.

11. Apparatus for facilitating performance of a surgical procedure, which comprises:
  probe means including a probe adapter and a probe coupled to the probe adapter, the probe adapted to move with respect to the probe adapter along a line parallel to a probe direction defined by the probe adapter, the probe having a probe tip for contacting a portion of an anatomy of a patient;
  digitizer means for providing positional data corresponding to the probe direction and a probe tip position;
  computer processing means for accepting the positional data and for accepting scanner image data of the portion of the anatomy; and
  computer display means for displaying the probe direction and the probe tip position with respect to the portion of the anatomy.

12. The apparatus according to claim 11 further including measuring means coupled to the probe means for measuring a relative position of the probe relative to the probe adapter.

* * * * *